United States Patent
David

(10) Patent No.: US 11,052,106 B2
(45) Date of Patent: Jul. 6, 2021

(54) HYPOTHERMAL INHALATION GAS COMPOSITION

(71) Applicant: MONATOMICS TECHNOLOGY, Aix en Provence (FR)

(72) Inventor: Hélène David, Saint-Laurent de l'Ile d'Orleans (CA)

(73) Assignee: MONATOMICS TECHNOLOGY, Aix en Provence (FR)

( * ) Notice: Subject to any disclaimer, the term of this patent is extended or adjusted under 35 U.S.C. 154(b) by 0 days.

(21) Appl. No.: 16/863,890

(22) Filed: Apr. 30, 2020

(65) Prior Publication Data

US 2020/0254010 A1 Aug. 13, 2020

Related U.S. Application Data

(62) Division of application No. 16/091,135, filed as application No. PCT/FR2016/050824 on Apr. 8, 2016, now abandoned.

(51) Int. Cl.
| | |
|---|---|
| *A61K 33/00* | (2006.01) |
| *A61F 7/00* | (2006.01) |
| *A61K 9/00* | (2006.01) |
| *A61K 45/06* | (2006.01) |
| *A61F 7/12* | (2006.01) |

(52) U.S. Cl.
CPC ............... *A61K 33/00* (2013.01); *A61F 7/00* (2013.01); *A61K 9/007* (2013.01); *A61K 45/06* (2013.01); *A61F 2007/006* (2013.01); *A61F 2007/126* (2013.01)

(58) Field of Classification Search
CPC .... A61K 33/00; A61K 2300/00; A61K 45/06; A61K 9/007; A61M 2202/0208; A61M 16/1075; A61M 16/12; A61M 2202/0007; A61M 2202/02; A61M 2202/025; A61M 2202/0291; A61M 2205/3368; A61M 2205/3606
See application file for complete search history.

(56) References Cited

U.S. PATENT DOCUMENTS

| | | |
|---|---|---|
| 5,099,834 A | 3/1992 | Fishman |
| 5,228,434 A | 7/1993 | Fishman |

FOREIGN PATENT DOCUMENTS

| | | | |
|---|---|---|---|
| FR | 2999082 A1 | 6/2014 | |
| RU | 2524765 C1 | 8/2014 | |
| WO | WO-2008122645 A2 * | 10/2008 | ......... G06F 21/6218 |
| WO | 2008132239 A1 | 11/2008 | |
| WO | 2010035074 A1 | 4/2010 | |
| WO | 2014167244 A1 | 10/2014 | |

OTHER PUBLICATIONS

Osipova et al. (Abstractor Problemy Kosmicheskoi Biologii, 1971;16:143-8) (Year: 1971).*
Written Opinion in corresponding PCT Application No. PCT/FR2016/050824, dated Dec. 6, 2016 (an English translation attached hereto).
International Search Report in corresponding PCT Application No. PCT/FR2016/050824, dated Dec. 6, 2016 (an English translation attached hereto).
International Preliminary Report on Patentability in corresponding PCT Application No. PCT/FR2016/050824, dated Oct. 9, 2018.
Tapper D, et al. "The effect of helium-oxygen mixtures on body temperature", Journal of pediatric surgery, vol. 9, 1974, pp. 597-603.
David, et al. "Post-ischemic helium provides neuroprotection in rats subjected to middle cerebral artery occlusion-induced ischemia by producing hypothermia." Journal of Cerebral Blood Flow & Metabolism 29.6 (2009): 1159-1165.

* cited by examiner

*Primary Examiner* — Ernst V Arnold
(74) *Attorney, Agent, or Firm* — Leason Ellis LLP

(57) ABSTRACT

The present application relates to methods to administer to a patient a hypothermal inhalation gas composition that includes oxygen and a mixture of inert gases. The mixture of inert gases includes a first compound selected from xenon and argon, and a second compound having hypothermal properties, such as helium. In the methods, a gas composition including oxygen and a mixture of inert gases is selected and the gas composition is administered to the patient at an inhalation temperature of a specified range such that the body temperature of the patient is maintained within a specified temperature range.

17 Claims, 2 Drawing Sheets

HYPOTHERMAL INHALATION GAS COMPOSITION

CROSS-REFERENCE TO RELATED APPLICATIONS

This application is a divisional application of U.S. patent application Ser. No. 16/091,135 filed Oct. 4, 2018, which claims priority to International Patent Application No. PCT/FR2016/050824, filed Apr. 8, 2016, which are hereby incorporated by reference in their respective entireties.

The present invention relates to an inhalation gas composition and more particularly to a selection of appropriate proportions of the gases of the composition.

In the case of ischemia followed by a reperfusion, and for example in the case of CVA (acronym for "cerebrovascular accident"), neonatal encephalopathy, or therapeutic ischemia such as ischemia due to an organ transplantation or to the placement of a clamp during a surgical intervention, in particular in cardiac surgery, it is conventional to set up a controlled hypothermia for the purpose of protecting the brain by reducing the cell metabolism.

Such a setting up of hypothermal conditions is still very often the only therapy proposed in the context of neurological (ischemic or non-ischemic) and psychiatric pathologies ("Drug Treatment in Psychiatry," Trevor Silverstone and Paul Turner Eds., 1995 (p. 291)).

Xenon is an anesthetic agent which has had a marketing authorization in Europe since 2007. It is probably as a glutaminergic receptor antagonist of the N-methyl-D-aspartate (NMDA) type and due to its anti-proteolytic effect that xenon has organoprotective and in particular neuroprotective properties ("Xenon: elemental anaesthesia in clinical practice," Robert D. Sanders, Daqing Ma and Mervyn Maze, British Medical Bulletin (2005) 71 (1): 115-135).

Studies have also shown that argon, a type A GABAergic receptor agonist ("Gamma-aminobutyric acid neuropharmacological investigations on narcosis produced by nitrogen, argon, or nitrous oxide," Abraini J H, Kriem B, Balon N, Rostain J C, Risso J J, Anesthesia and Analgesia 2003; 96:746-9) and mu type opioidergic receptor antagonist ("Argon blocks the expression of locomotor sensitization to amphetamine through antagonism at the vesicular monoamine transporter-2 and mu-opioid receptor in the nucleus accumbens," David H N, Dhilly M, Degoulet M, Poisnel G, Meckler C, Vallée N, Blatteau J É, Risso J J, Lemaire M, Debruyne D, Abraini J H, Translational Psychiatry 2015; 5:e594), has organoprotective and in particular neuroprotective properties ("Argon: Systematic Review on Neuro- and Organoprotective Properties of an "Inert" Gas," A. Höllig, A. Schug, A V. Fahlenkamp, R. Rossaint, M. Coburn and Argon Organo-Protective Network (AON), International Journal of Molecular Sciences, 2014 October; 15(10): 18175-18196)).

However, xenon and argon have the disadvantage of having hyperthermal properties for certain inhalation temperatures, these inert gases having a higher molecular weight than that of nitrogen and a lower thermal conductivity than that of nitrogen, which gives them a hyperthermal character when they are used in inhalation gas compositions. Now the use of a gas with hyperthermal properties will tend to put the subjects who inhale it in a state of hyperthermia, which is detrimental in the context of the therapies of most neurological or psychiatric diseases.

It results from this that the use of xenon or argon would require a parallel cooling of the subject inhaling these inert gases, in particular by independent mechanical cooling means, in order to reach a general state of hypothermia.

These independent cooling means such as bags of water or cold gel are applied directly on the body or the area to be cooled. The independent cooling means can also consist of the use of a hydraulic pad with adjustable temperature or of selective cooling carried out with the aid of a refrigerated water circuit. However, such cooling means by direct application on the skin do not make it possible to achieve an optimal cooling of the subject, that is to say a homogeneous cooling, it being understood that a temperature gradient forms between the skin in contact with the cooling means and the internal organs.

In this context, the subject matter of the invention is thus an inhalation gas composition including oxygen and a mixture of inert gases. The mixture of inert gases includes a first compound selected from xenon and argon having hyperthermal properties, and a second compound having hypothermal properties, said mixture of inert gases comprising proportions of the first compound and of the second compound such that said mixture of inert gases is hypothermal under predetermined temperature conditions.

"Inhalation" gas composition is understood to mean a gas composition including at least 21% oxygen, so that it can be inhaled by a subject, it being understood that with less than 21% oxygen in the inhalation mixture, the subject is in a state of hypoxia.

Echoing what was defined above, it is understood that a gas or a mixture of inert gases having hypothermal properties is defined as being a gas or a mixture having a lower molecular weight than that of nitrogen and a higher thermal conductivity than that of nitrogen, which thus gives it the possibility of putting the subject inhaling said gas or mixture in a state of hypothermia. In other words, the gas composition inhaled at a certain temperature makes it possible to maintain the body temperature of the subjects inhaling it within a so-called hypothermal temperature range below 36° C. and more precisely from 32° C. to 35° C.

It is understood that the inhalation of such a composition for inhalation temperatures between 16° C. and 27° C. makes it possible to maintain a hypothermia of the body, that is to say to maintain a body temperature in a hypothermal range, that is to say a range of temperatures below the range of normal variability of the body, roughly between 36.1° C. and 37.8° C. (Simmers, Louise. Diversified Health Occupations, 2nd ed. Canada: Delmar, 1988: 150-151), it being possible to round off this range to 36-38° C. or 37±1° C. In general, the therapeutic hypothermal range extends to below 36° C. and more specifically between 32° C. and 35° C. In other words, the invention makes it possible to provide a gas composition which does not generate or does not risk generating an increase in the body temperature of subjects inhaling the composition outside of a range of so-called hypothermal values extending below 36° C. and more specifically from 32° C. to 35° C.

In addition, this gas composition makes it possible to avoid the temperature gradient between the skin and the internal organs that occurs with the use of mechanical cooling means. In other words, the inhalation gas composition makes it possible to achieve an optimal cooling of the subject, that is to say homogeneous cooling.

According to a feature of the invention, the second compound having hypothermal properties also has organoprotective properties. Organoprotective properties are understood to mean the protection of internal organs such as, for example, the brain, blood vessels and nerves. Thus, in addition to maintaining the body temperature in a range of values corresponding to a therapeutic hypothermia of the body, the inhalation gas composition according to the invention makes it possible to protect the internal organs when it is inhaled by a subject.

More precisely, the second compound can advantageously be helium. In fact, helium has both hypothermal and organoprotective properties ("Heliox and oxygen reduce infarct volume in a rat model of focal ischemia," Pan Y, Zhang H, Van Deripe D R, Cruz-Flores S, Pannerton W M (2007), Experimental Neurology 205:587-90; "The effect of helium-oxygen mixtures on body temperature," Tapper D, Arensman R, Johnson C, Folkman J (1974), Journal of Pediatric Surgery 9:597-603; "Post-ischemic helium provides neuroprotection in rats subjected to middle cerebral artery occlusion-induced ischemia by producing hypothermia," David N H, Haelewyn B, Chazalviel L, Lecocq M, Degoulet M, Risso J J, Abraini J H (2009), Journal of Cerebral Blood Flow & Metabolism 29:1159-1165; "Modulation by the Noble Gas Helium of Tissue Plasminogen Activator: Effects in a Rat Model of Thromboembolic Stroke," Haelewyn B, David H N, Blatteau J E, Vallée N, Meckler C, Risso J J, Abraini J H (2016), Critical Care Medicine in press).

The inhalation gas composition includes 50% to 79% of the mixture of inert gases; these proportions make it possible to ensure that the composition can be inhaled and to avoid hypoxia of the subject inhaling the composition.

According to a first series of features of the invention, taken alone or in combination, in the case of application of a first compound in the form of xenon, one can provide that:
said composition includes at least 13% helium.
said composition includes at most 50% xenon. Limiting the xenon content to less than 50% makes it possible to avoid an anesthetic effect on the subject inhaling the composition, while at the same time limiting the costs of obtaining the composition.

According to an embodiment of the invention, for inhalation temperatures less than or equal to 22° C., one can provide that said composition includes 21% to 25% oxygen, 43% to 48% helium, and 30% to 35% xenon.

More precisely, for an oxygen level of 22%, the composition can include 45% to 47% helium and 31% to 33% of xenon, or for an oxygen level of 25%, it can include 43% to 45% helium and 30% to 32% xenon, in order to ensure a body temperature between 32° C. and 35° C. in humans. As an example, in order to ensure a body temperature of 34° C., said composition can include roughly 22% oxygen, 43% helium, and 35% xenon. Roughly is understood to mean that a margin of error or uncertainty of 1% is acceptable.

According to a second series of features of the invention, taken alone or in combination, in the case of application of a first compound in the form of argon, one can provide that:
said composition includes at least 11% helium.
said composition includes at most 67% argon.

According to an embodiment of the invention, one can provide that said composition includes 21% to 25% oxygen, 22% to 76% helium, and 2% to 56% argon.

More precisely, when the composition is inhaled at a temperature of 22° C., it can include 22% oxygen, 37% to 68% helium, and 10% to 41% argon, or said composition includes 25% oxygen, 36% to 65% helium, and 10% to 39% argon, in order to ensure a body temperature between 33° C. and 35° C. in humans.

BRIEF DESCRIPTION OF THE DRAWING FIGURES

Other features, details and advantages of the invention will become clearer upon reading the description given below for information in connection with drawings in which.

Figure 1:
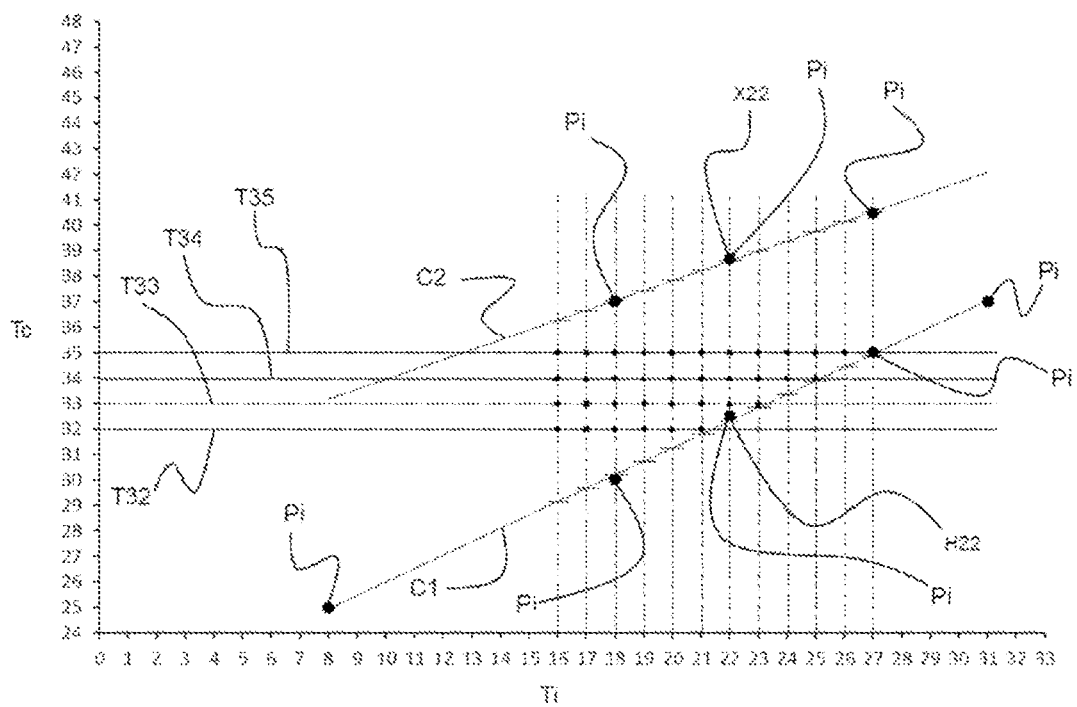
FIG. 1 is a graphic representation of the rat body temperature as a function of the temperature of the inhaled gas which is helium (curve C1) or xenon (curve C2)

appended table 1 represents the physical properties of the compounds of the present invention;

appended table 2 represents the proportions of xenon and of helium as a function of the proportion of oxygen, of the temperature of inhalation of the composition and of its effect on the body temperature measured in rats;

appended table 3 represents the proportions of argon and of helium as a function of the proportion of oxygen, of the temperature of inhalation of the composition and of its effect on the body temperature measured in rats.

The air consists mainly of 21% oxygen, 78% nitrogen, and 1% rare gas. It is roughly equivalent to say that the reference air consists of 21% oxygen and 79% nitrogen, this oxygen content being the minimum value that a gas mixture has to contain to avoid hypoxia in a subject inhaling such a gas mixture. The gas composition according to the invention comprises oxygen and a mixture of inert gases, the proportion of nitrogen in the air being replaced by the mixture of inert gases.

This mixture of inert gases consists of a first compound having hyperthermal properties and of a second compound having hypothermal properties. The proportions of each compound of the mixture of inert gases are such that they enable the inhaled gas composition to maintain the body temperature of a subject within a so-called hypothermal temperature range from 32° C. to 35° C.

The composition contains at least 21% oxygen, in order to avoid any hypoxia during its inhalation. The composition contains at most 50% oxygen, and preferably between 21% and 30%, and even between 21% and 25%. The composition thus contains at least 50% of a mixture of inert gases, and preferably 70% to 79%.

The mixture of inert gases includes a first compound selected from inert gases having hyperthermal properties and a second compound selected from inert gases having hypothermal properties. The inert gases have the advantage of not being metabolized after they have been inhaled.

The first compound selected from the inert gases with hyperthermal properties is xenon or argon. In fact, as shown in the appended table 1, xenon and argon have a higher molecular weight than nitrogen and a lower thermal conductivity than nitrogen, which gives them a hyperthermal character when either of the two replaces nitrogen in a gas mixture.

In addition to having hyperthermal properties, xenon and argon have organoprotective properties, that is to say that these compounds enable the protection of organs, blood vessels and nerves. These compounds are capable of protecting the brain in particular.

Below, a first embodiment of the invention is described, in which the gas composition includes xenon as first compound, that is to say as compound having the hyperthermal properties.

Xenon is then mixed with a gas having hypothermal properties in proportions such that the mixture has hypothermal properties. Below, an inert gas which is particular in that it has hypothermal properties, namely helium, is selected to be mixed with xenon. In fact, as appended table 1 shows, helium has a lower molecular weight than nitrogen and a higher thermal conductivity than nitrogen, which gives it a hypothermal character when it replaces nitrogen in a gas mixture. Moreover, helium also has organoprotective properties.

In order to offer a gas composition which is hypothermal, that is to say which does not change the body temperature of subjects inhaling the composition outside of a temperature bracket between 32° C. and 35° C., the proportions of the first compound and of the second compound of the mixture of inert gases have to be precisely calculated. These proportions are extrapolated in particular from experimental data obtained with gases constituting the mixture. These experimental data, obtained in rats whose so-called normal body temperature is close to that of humans, namely between 35.9° C. and 37.5° C. (Animal care and use committee, Johns Hopkins University, web.jhu.edu), made it possible to prepare the graphs of FIGS. 1 and 2.

The graph of FIG. 1, which represents the experimental body temperature data Tc collected on rats as a function of the inhalation temperature Ti of a helium-oxygen mixture (curve C1) or of a xenon-oxygen mixture (curve C2), makes it possible to determine the proportions of the gas composition to be complied with in order to obtain a hypothermal gas mixture, depending on the inhalation temperature. In a more detailed manner, curves C1 and C2 correspond to regression lines obtained based on said experimental data Pi, several examples of which have been plotted in FIG. 1.

The experimental data were obtained as follows: The rats were placed for 3 hours in a closed enclosure supplied with a continuous flow of a gas mixture containing 22% oxygen ($O_2$) and 78% helium, xenon or argon (He, Xe or Ar). This gas mixture was administered at different temperatures. The flow of the gas mixture was 10 mL/min and made it possible to maintain the carbon dioxide ($CO_2$) concentration below 0.03% and the humidity at around 60% to 70%. The gas mixtures were obtained with the aid of mass flow meters having an absolute precision of 0.2% of the displayed value (for example, displayed value 78%, precision=0.16% or 78+/−0.16%); the oxygen concentration was checked with the aid of a specific analyzer. At the end of the 3 hours of exposure, the rectal body temperature of the rats was measured for each administration temperature.

Since rats are ordinarily used as a preclinical model for the study of human physiology and pathologies, and given moreover that the normal body temperatures Tc of rats and humans are of the same order of magnitude, the administration of a gas mixture at different temperatures in rats in a closed enclosure is thus comparable to the administration in humans of such a gas mixture at an inhalation temperature Ti which is roughly equal to the ambient temperature of the room in which the gas treatment is administered. The inhalation temperature Ti can be between 16° C. and 27° C., for example.

For an inhalation temperature of 22° C., one determines:
points H22 and X22 located on the helium curve C1 and the xenon curve C2, respectively;
horizontal lines T32, T33, T34 and T35 corresponding to target temperatures of 32° C., 33° C., 34° C. and 35° C.

In this way, for a distance H22-X22 representing the sum of the percentages of helium and xenon in the inhalation gas mixture including oxygen, xenon and helium, one gets:
a distance X22-T33 which represents the proportion of helium making it possible to maintain the body temperature Tc at 33° C.,
a distance H22-T33 which represents the proportion of xenon making it possible to maintain the body temperature at 33° C.,
a distance X22-T34 which represents the proportion of helium making it possible to maintain the body temperature at 34° C.,
a distance H22-T34 which represents the proportion of xenon making it possible to maintain the body temperature at 34° C.,
a distance X22-T35 which represents the proportion of helium making it possible to maintain the body temperature at 35° C.,
a distance H22-T35 which represents the proportion of xenon making it possible to maintain the body temperature at 35° C.

These experimental data thus made it possible to prepare table 2, presented in an appendix, which includes the proportions of a mixture of helium and xenon, while taking into account the proportion of oxygen. It is clearly apparent that these proportions of helium and xenon depend both on the temperature of the inhaled gas Ti, on the proportion of oxygen present in the gas composition, and on the body temperature Tc that one wishes to obtain. One then observes that the higher the inhalation temperature Ti, the higher the proportion of helium is for maintaining the body temperature Tc in a hypothermal temperature range set at below 36° C. and more specifically between 32° C. and 35° C.

More precisely, the distance H22-X22 corresponds to the difference between a body temperature of a rat inhaling an oxygen-helium mixture and a body temperature of a rat inhaling an oxygen-xenon mixture, at the same inhalation temperature of 22° C. The distance X22-T34 corresponds to the difference between a body temperature of rat inhaling an oxygen-xenon mixture at an inhalation temperature of 22° C. and a target body temperature of 34° C. In the same way, for an inhalation temperature of 22° C., the distances X22-T32, X22-T33 and X22-T35 correspond to the difference between the body temperature of the rat inhaling the oxygen-xenon mixture and the target body temperatures of 32° C. to 35° C.

Taking into account the functions represented by the regression lines C1, C2, the proportions of the gas mixture to be complied with in order to obtain a hypothermal mixture were determined according to the calculation method described below.

Curve C1 represents the function y=0.526x+20.748 and curve 2 represents the function y=0.3877x+30.075. For example, let us take the case in which one wishes to obtain a body temperature of 34° C. with an ambient temperature of 22° C. and an oxygen level of 22%, that is to say a level of inert gases of 78%:

A first step consists of a calculation of the body temperatures: for an inhalation temperature roughly equal to 22° C., when a 22% $O_2$-78% He mixture is inhaled, one gets a body temperature of 32.32° C. using the function representative of curve C1, and when a 22% $O_2$-78% Xe mixture is inhaled, one gets a body temperature of 38.60° C. using the function representative of curve C2.

From this one derives, in a second step, a difference, for the inhalation temperature of 22° C., between the body temperatures obtained by the calculations in the first step, which will subsequently be used as reference value for the calculations of the content of each of the compounds of the mixture: a first difference D1 is thus calculated between the body temperature obtained with a 22% $O_2$-78% Xe mixture and the body temperature obtained with a 22% $O_2$-78% He mixture, and, in the case described with an inhalation temperature equal to 22° C., a value of 6.28 is obtained here.

A third step consists of a calculation of the content of one of the gases to be provided in order to ensure a body temperature of 34° C. for an inhalation temperature of 22° C. In the case described, one arbitrarily chooses to determine the helium content, it being understood that one could choose to first determine the xenon content. A second difference D2 is calculated between the body temperature obtained with a 22% O$_2$-78% Xe mixture and the body temperature desired for this inhalation temperature of 22° C., giving a value of 4.6 in this case.

This ratio between the values calculated in the second and third steps is used in a cross product calculation in order to determine the helium content, relative to the 78% of inert gases in addition to oxygen, of the gas composition to be prepared in order to obtain a body temperature of 34° C.: In the case described, a content equal to 57% (4.6×78/6.28)% is obtained here. From this, the xenon content is derived by subtraction (78−57=21), and, in the present case, the composition then will consist of 57% helium, 22% oxygen, and 21% xenon.

According to this example and upon reading table 2, for an inhalation temperature Ti of 22° C., an oxygen proportion of 22%, and a desired body temperature between 32° C. and 35° C., the composition includes 8 to 33% xenon and 45 to 70% helium. More precisely, if one wishes to achieve a body temperature of 34° C., the composition includes 22% oxygen, 56% to 58% helium, and 20% to 22% xenon.

One also observes that, in all the cases, the composition includes at least 9% helium and at most 65% xenon. More particularly, when the oxygen content is between 21 and 30%, the composition includes at least 13% helium and at most 65% xenon. According to the present invention, the aim is a gas composition enabling, on the one hand, the presence of the target thermal properties, that is to say the thermal properties obtained with the aid of a hypothermal mixture of inert gases, it being possible to read in the tables the appropriate proportions for obtaining such a composition, and, according to the present invention, the aim is a composition enabling, on the other hand, a use on subjects without risk of undesired anesthetic effect, that is to say by limiting the addition of xenon to a maximum of 50%. In addition, for inhalation temperatures Ti between 19° C. and 23° C., the composition includes 21 to 30% oxygen, 26 to 77% helium, and 2 to 50% xenon. Preferably, for inhalation temperatures less than or equal to 22° C., the composition includes 22% oxygen, 45% to 47% helium, and 31% to 33% xenon.

In the same manner as described above, the graph of FIG. 2 represents the experimental data Pi of the body temperature obtained in rats as a function of the temperature of inhalation of helium (curve C1) or of argon (curve C3), based on which the proportions of the different gases in a helium-argon-oxygen mixture were calculated (table 3). As examples, the reference points A18 and H18 used in this case were taken at an inhalation temperature Ti of 18° C., and the distances with the target body temperatures T32, T33, T34 and T35 are thus representative of the proportions of the mixture of inert gases for this inhalation temperature of 18° C.

Figure 2:
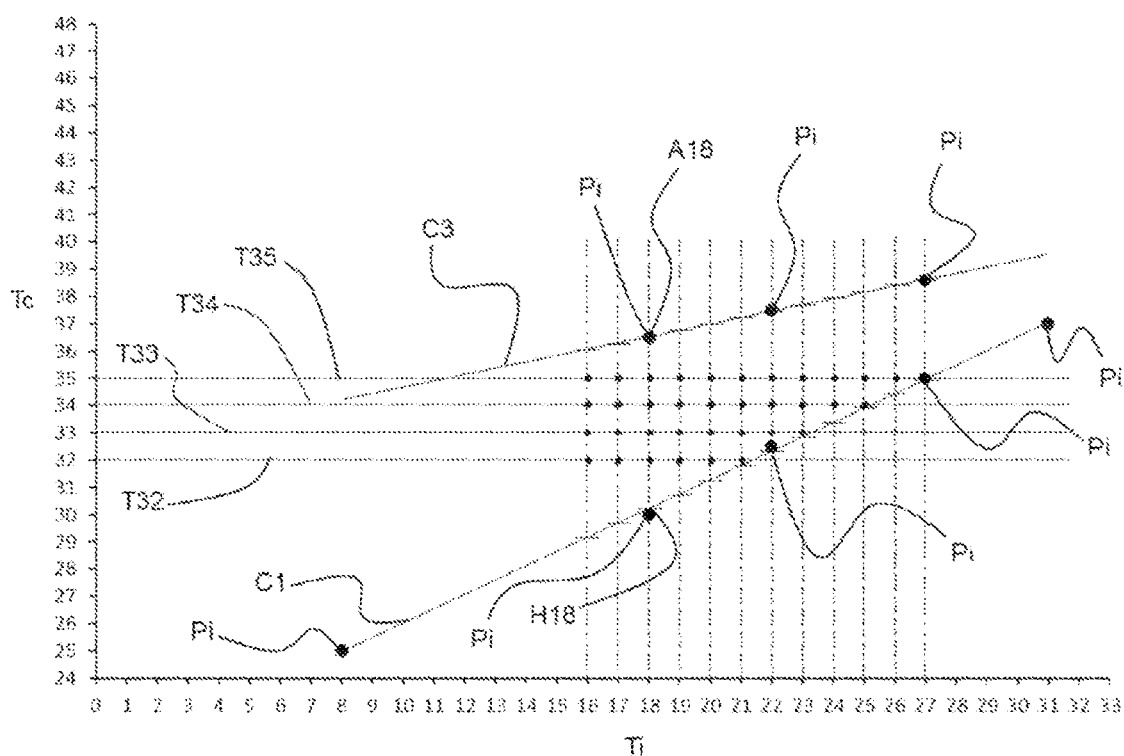
FIG. 2 is a graphic representation of the rat body temperature as a function of the temperature of the inhaled gas which is helium (curve C1) or argon (curve C3)

A comparison between the graphs of FIGS. 1 and 2 shows that curve C3 has a smaller slope than curve C2. In fact, curve C2 represents the function y=0.3877x+30.075, whereas curve C3 represents the function y=0.2328x+32.334, the argon having lower hyperthermal properties than xenon. Thus, the proportions of the inert gases in the inhalation gas composition according to the invention vary as a function of the quality of the first compound used in this composition, which is selected from argon or xenon.

Upon reading table 3, one observes that in all the cases the composition includes at most 67% argon and at least 8% helium. More particularly, when the oxygen content is between 21 and 30%, the composition includes at most 67% argon and at least 11% helium. In addition, for inhalation temperatures Ti between 19° C. and 23° C., the composition includes 21 to 30% oxygen, 20 to 76% helium, and 2 to 56% argon. And again for inhalation temperatures Ti of between 19° C. and 23° C., the composition includes 21 to 25% oxygen, 22% to 76% helium, and 2% to 56% argon.

Finally, these proportions make it possible to ensure that the mixture of inert gases is hypothermal. When the gas composition is inhaled at a given temperature Ti, it makes it possible to maintain the body temperature Tc of the subject inhaling it within a so-called hypothermal body temperature range from 32° C. to 35° C., while avoiding a body temperature gradient between the skin and the internal organs.

In a non-limiting manner, the inhalation of such a composition can be carried out by means of a human-machine interface such as a respiratory ventilator, a face mask, respiratory goggles or any other type of interface.

Moreover, in order to avoid inhalation of just one or some of the inert gases, the packaging of such a composition is preferably carried out in a single container with the three compounds, namely xenon or argon, helium, and oxygen, in pre-established proportions under a pressure between 10 and 300 bar. The container has a volume of 0.1 L to 50 L. This packaging in a single bottle is referred to as "ready-to-use." In order to ensure a proportion of at least 21% oxygen in the composition and still obtain an inhalation gas composition, taking into account an uncertainty of 1% between the different steps existing between the manufacturing, the packaging and the administration of the gas composition, and in order to avoid hypoxia for the subject to whom the mixture is administered, the oxygen proportion in this type of packaging is always at least 22%.

TABLE 1

|  | Chemical element | | | |
| --- | --- | --- | --- | --- |
|  | Nitrogen (N) | Xenon (Xe) | Argon (Ar) | Helium (He) |
| Molecular weight (mg/mol) | 28.013 | 131.29 | 39.948 | 4.003 |
| Thermal conductivity (mW/m · K) | 24.001 | 5.107 | 16.483 | 146.20 |

TABLE 2

| | % O2 = 21 | | | | | | | | % O2 = 22 | | | | | | |
| --- | --- | --- | --- | --- | --- | --- | --- | --- | --- | --- | --- | --- | --- | --- | --- |
| | TC = 35° C. | | TC = 34° C. | | TC = 33° C. | | TC = 32° C. | | TC = 35° C. | | TC = 34° C. | | TC = 33° C. | |
| Ti | % He | % Xe | % He | % Xe | % He | % Xe | % He | % Xe | % He | % Xe | % He | % Xe | % He | % Xe |
| 16 | 14 | 65 | 25 | 54 | 36 | 43 | 48 | 31 | 14 | 64 | 25 | 53 | 36 | 42 |
| 17 | 19 | 60 | 30 | 49 | 42 | 37 | 53 | 26 | 19 | 59 | 30 | 48 | 41 | 37 |
| 18 | 24 | 55 | 35 | 44 | 47 | 32 | 58 | 21 | 23 | 55 | 35 | 43 | 46 | 32 |

TABLE 2-continued

| Ti | | | | | | | | | | | | | |
|----|----|----|----|----|----|----|----|----|----|----|----|----|----|
| 19 | 29 | 50 | 41 | 38 | 52 | 27 | 64 | 15 | 28 | 50 | 40 | 38 | 52 | 26 |
| 20 | 34 | 45 | 46 | 33 | 58 | 21 | 70 | 9  | 34 | 44 | 46 | 32 | 57 | 21 |
| 21 | 40 | 39 | 52 | 27 | 64 | 15 | 76 | 3  | 39 | 59 | 51 | 27 | 63 | 15 |
| 22 | 45 | 34 | 58 | 21 | 70 | 9  |    |    | 45 | 33 | 57 | 21 | 70 | 8  |
| 23 | 51 | 28 | 64 | 15 | 77 | 2  |    |    | 51 | 27 | 63 | 15 | 76 | 2  |
| 24 | 58 | 21 | 71 | 8  |    |    |    |    | 57 | 21 | 70 | 8  |    |    |
| 25 | 64 | 15 | 78 | 1  |    |    |    |    | 63 | 15 | 77 | 1  |    |    |
| 26 | 71 | 8  |    |    |    |    |    |    | 70 | 8  |    |    |    |    |
| 27 | 78 | 1  |    |    |    |    |    |    | 77 | 1  |    |    |    |    |

| | % O2 = 22 | | % O2 = 23 | | | | | | | | |
|---|---|---|---|---|---|---|---|---|---|---|---|
| | TC = 32° C. | | TC = 35° C. | | TC = 34° C. | | TC = 33° C. | | TC = 32° C. | |
| Ti | % He | % Xe | % He | % Xe | % He | % Xe | % He | % Xe | % He | % Xe |
| 16 | 47 | 31 | 14 | 63 | 25 | 52 | 35 | 42 | 46 | 31 |
| 17 | 52 | 26 | 18 | 59 | 29 | 48 | 40 | 37 | 52 | 25 |
| 18 | 58 | 20 | 23 | 54 | 34 | 43 | 46 | 31 | 57 | 20 |
| 19 | 63 | 15 | 28 | 49 | 40 | 37 | 51 | 26 | 63 | 14 |
| 20 | 69 | 9  | 33 | 44 | 45 | 32 | 57 | 20 | 68 | 9  |
| 21 | 75 | 3  | 39 | 38 | 51 | 26 | 63 | 14 | 75 | 2  |
| 22 |    |    | 44 | 33 | 56 | 21 | 69 | 8  |    |    |
| 23 |    |    | 50 | 27 | 63 | 14 | 75 | 2  |    |    |
| 24 |    |    | 56 | 21 | 69 | 8  |    |    |    |    |
| 25 |    |    | 63 | 14 | 76 | 1  |    |    |    |    |
| 26 |    |    | 69 | 8  |    |    |    |    |    |    |
| 27 |    |    | 76 | 1  |    |    |    |    |    |    |

| | % O2 = 24 | | | | | | | | % O2 = 25 | | | | |
|---|---|---|---|---|---|---|---|---|---|---|---|---|---|
| | TC = 35° C. | | TC = 34° C. | | TC = 33° C. | | TC = 32° C. | | TC = 35° C. | | TC = 34° C. | | TC = 33° C. | |
| Ti | % He | % Xe | % He | % Xe | % He | % Xe | % He | % Xe | % He | % Xe | % He | % Xe | % He | % Xe |
| 16 | 14 | 62 | 24 | 52 | 35 | 41 | 46 | 30 | 13 | 62 | 24 | 51 | 35 | 40 |
| 17 | 18 | 58 | 29 | 47 | 40 | 36 | 51 | 25 | 18 | 57 | 29 | 46 | 39 | 36 |
| 18 | 23 | 53 | 34 | 42 | 45 | 51 | 56 | 20 | 23 | 52 | 33 | 42 | 44 | 31 |
| 19 | 28 | 48 | 39 | 37 | 50 | 26 | 62 | 14 | 27 | 48 | 39 | 36 | 58 | 25 |
| 20 | 33 | 43 | 44 | 32 | 56 | 20 | 68 | 8  | 32 | 43 | 44 | 31 | 55 | 20 |
| 21 | 38 | 38 | 50 | 26 | 62 | 14 | 74 | 2  | 38 | 37 | 49 | 26 | 61 | 14 |
| 22 | 44 | 32 | 56 | 30 | 68 | 8  |    |    | 43 | 32 | 55 | 20 | 67 | 8  |
| 23 | 49 | 27 | 62 | 14 | 74 | 2  |    |    | 49 | 26 | 61 | 14 | 73 | 2  |
| 24 | 55 | 21 | 68 | 8  |    |    |    |    | 55 | 28 | 67 | 8  |    |    |
| 25 | 62 | 14 | 75 | 1  |    |    |    |    | 61 | 14 | 74 | 1  |    |    |
| 26 | 68 | 8  |    |    |    |    |    |    | 67 | 8  |    |    |    |    |
| 27 | 75 | 1  |    |    |    |    |    |    | 74 | 1  |    |    |    |    |

| | % O2 = 25 | | % O2 = 26 | | | | | | | | |
|---|---|---|---|---|---|---|---|---|---|---|---|
| | TC = 32° C. | | TC = 35° C. | | TC = 34° C. | | TC = 33° C. | | TC = 32° C. | |
| Ti | % He | % Xe | % He | % Xe | % He | % Xe | % He | % Xe | % He | % Xe |
| 16 | 45 | 30 | 13 | 61 | 24 | 50 | 34 | 40 | 45 | 29 |
| 17 | 50 | 25 | 18 | 56 | 28 | 46 | 39 | 35 | 49 | 25 |
| 18 | 55 | 20 | 22 | 52 | 33 | 41 | 44 | 30 | 55 | 19 |
| 19 | 61 | 14 | 27 | 47 | 38 | 36 | 49 | 25 | 60 | 14 |
| 20 | 67 | 8  | 32 | 42 | 43 | 31 | 54 | 20 | 66 | 8  |
| 21 | 73 | 2  | 38 | 37 | 49 | 25 | 60 | 14 | 72 | 2  |
| 22 |    |    | 42 | 32 | 54 | 20 | 66 | 8  |    |    |
| 23 |    |    | 48 | 26 | 60 | 14 | 72 | 2  |    |    |
| 24 |    |    | 54 | 20 | 66 | 8  |    |    |    |    |
| 25 |    |    | 60 | 14 | 73 | 1  |    |    |    |    |
| 26 |    |    | 67 | 7  |    |    |    |    |    |    |
| 27 |    |    | 73 | 1  |    |    |    |    |    |    |

| | % O2 = 27 | | | | | | | | % O2 = 28 | | | | |
|---|---|---|---|---|---|---|---|---|---|---|---|---|---|
| | TC = 35° C. | | TC = 34° C. | | TC = 33° C. | | TC = 32° C. | | TC = 35° C. | | TC = 34° C. | | TC = 33° C. | |
| Ti | % He | % Xe | % He | % Xe | % He | % Xe | % He | % Xe | % He | % Xe | % He | % Xe | % He | % Xe |
| 16 | 13 | 60 | 23 | 50 | 34 | 59 | 44 | 29 | 13 | 59 | 23 | 49 | 33 | 39 |
| 17 | 17 | 56 | 28 | 45 | 38 | 35 | 49 | 24 | 17 | 55 | 28 | 44 | 38 | 34 |
| 18 | 22 | 51 | 33 | 40 | 43 | 30 | 54 | 19 | 22 | 50 | 32 | 40 | 43 | 29 |
| 19 | 27 | 46 | 37 | 36 | 48 | 25 | 59 | 14 | 26 | 46 | 37 | 35 | 48 | 24 |
| 20 | 31 | 42 | 43 | 30 | 54 | 19 | 65 | 8  | 31 | 41 | 42 | 30 | 53 | 19 |
| 21 | 37 | 36 | 48 | 25 | 59 | 14 | 71 | 2  | 36 | 36 | 47 | 25 | 58 | 14 |
| 22 | 42 | 31 | 53 | 30 | 65 | 8  |    |    | 41 | 31 | 53 | 19 | 64 | 8  |

TABLE 2-continued

| Ti | % He | % Xe | % He | % Xe | % He | % Xe | % He | % Xe | % He | % Xe | % He | % Xe |
|---|---|---|---|---|---|---|---|---|---|---|---|---|
| 23 | 47 | 26 | 59 | 14 | 71 | 2 | | | 47 | 25 | 58 | 14 | 70 | 2 |
| 24 | 53 | 20 | 65 | 8 | | | | | 52 | 20 | 64 | 8 | | |
| 25 | 59 | 14 | 72 | 1 | | | | | 58 | 14 | 71 | 1 | | |
| 26 | 66 | 7 | | | | | | | 65 | 7 | | | | |
| 27 | 72 | 1 | | | | | | | 71 | 1 | | | | |

| | % O2 = 28 | | % O2 = 29 | | | | | | | | |
|---|---|---|---|---|---|---|---|---|---|---|---|
| | TC = 32° C. | | TC = 35° C. | | TC = 34° C. | | TC = 33° C. | | TC = 32° C. | |
| Ti | % He | % Xe | % He | % Xe | % He | % Xe | % He | % Xe | % He | % Xe |
| 16 | 43 | 29 | 13 | 58 | 23 | 48 | 33 | 38 | 43 | 28 |
| 17 | 48 | 24 | 17 | 54 | 27 | 44 | 37 | 34 | 47 | 24 |
| 18 | 53 | 19 | 21 | 50 | 32 | 39 | 42 | 29 | 52 | 19 |
| 19 | 58 | 14 | 26 | 45 | 36 | 35 | 47 | 24 | 58 | 13 |
| 20 | 64 | 8 | 31 | 40 | 41 | 30 | 52 | 19 | 63 | 8 |
| 21 | 70 | 2 | 36 | 35 | 47 | 24 | 58 | 13 | 69 | 2 |
| 22 | | | 41 | 30 | 52 | 19 | 63 | 8 | | |
| 23 | | | 46 | 25 | 58 | 13 | 69 | 2 | | |
| 24 | | | 52 | 19 | 64 | 7 | | | | |
| 25 | | | 58 | 13 | 70 | 1 | | | | |
| 26 | | | 64 | 7 | | | | | | |
| 27 | | | 70 | 1 | | | | | | |

| | % O2 = 30 | | | | | | | | % O2 = 35 | | | |
|---|---|---|---|---|---|---|---|---|---|---|---|---|
| | TC = 35° C. | | TC = 34° C. | | TC = 33° C. | | TC = 32° C. | | TC = 35° C. | | TC = 34° C. | | TC = 33° C. |
| Ti | % He | % Xe | % He | % Xe | % He | % Xe | % He | % Xe | % He | % Xe | % He | % Xe | % He | % Xe |
| 16 | 13 | 57 | 22 | 48 | 32 | 38 | 42 | 28 | 12 | 53 | 21 | 44 | 30 | 35 |
| 17 | 17 | 53 | 27 | 43 | 37 | 33 | 47 | 23 | 16 | 49 | 25 | 40 | 34 | 31 |
| 18 | 21 | 49 | 31 | 39 | 41 | 29 | 52 | 18 | 20 | 45 | 29 | 38 | 39 | 26 |
| 19 | 26 | 44 | 36 | 34 | 46 | 24 | 57 | 13 | 24 | 41 | 33 | 32 | 43 | 22 |
| 20 | 30 | 40 | 41 | 29 | 52 | 18 | 62 | 8 | 28 | 37 | 38 | 27 | 48 | 17 |
| 21 | 35 | 35 | 46 | 24 | 57 | 13 | 68 | 2 | 33 | 32 | 43 | 22 | 53 | 12 |
| 22 | 40 | 30 | 51 | 19 | 62 | 8 | | | 37 | 28 | 48 | 17 | 58 | 7 |
| 23 | 45 | 25 | 57 | 13 | 68 | 2 | | | 42 | 23 | 53 | 12 | 63 | 2 |
| 24 | 51 | 19 | 63 | 7 | | | | | 47 | 18 | 58 | 7 | | |
| 25 | 57 | 13 | | 1 | | | | | 53 | 12 | 64 | 1 | | |
| 26 | 63 | 7 | | | | | | | 58 | 7 | | | | |
| 27 | 69 | 1 | | | | | | | 64 | 1 | | | | |

| | % O2 = 35 | | % O2 = 40 | | | | | | | |
|---|---|---|---|---|---|---|---|---|---|---|
| | TC = 32° C. | | TC = 35° C. | | TC = 34° C. | | TC = 33° C. | | TC = 32° C. | |
| Ti | % He | % Xe | % He | % Xe | % He | % Xe | % He | % Xe | % He | % Xe |
| 16 | 39 | 26 | 11 | 49 | 19 | 41 | 25 | 32 | 36 | 24 |
| 17 | 43 | 22 | 14 | 46 | 23 | 37 | 32 | 28 | 40 | 20 |
| 18 | 48 | 17 | 18 | 42 | 27 | 33 | 36 | 24 | 44 | 16 |
| 19 | 33 | 12 | 22 | 38 | 31 | 29 | 40 | 20 | 49 | 11 |
| 20 | 58 | 7 | 26 | 34 | 35 | 25 | 44 | 16 | 53 | 7 |
| 21 | 63 | 2 | 30 | 30 | 39 | 21 | 49 | 11 | 58 | 2 |
| 22 | | | 34 | 26 | 44 | 16 | 54 | 6 | | |
| 23 | | | 39 | 21 | 49 | 11 | 58 | 2 | | |
| 24 | | | 44 | 16 | 54 | 6 | | | | |
| 25 | | | 49 | 11 | 59 | 1 | | | | |
| 26 | | | 54 | 6 | | | | | | |
| 27 | | | 59 | 1 | | | | | | |

| | % O2 = 45 | | | | | | | | % O2 = 50 | | | | | | |
|---|---|---|---|---|---|---|---|---|---|---|---|---|---|---|---|
| | TC = 35° C. | | TC = 34° C. | | TC = 33° C. | | TC = 32° C. | | TC = 35° C. | | TC = 34° C. | | TC = 33° C. | | TC = 32° C. |
| Ti | % He | % Xe | % He | % Xe | % He | % Xe | % He | % Xe | % He | % Xe | % He | % Xe | % He | % Xe | % He | % Xe |
| 16 | 10 | 45 | 18 | 37 | 25 | 30 | 33 | 22 | 9 | 41 | 16 | 34 | 23 | 27 | 30 | 20 |
| 17 | 13 | 42 | 21 | 34 | 29 | 26 | 37 | 18 | 12 | 38 | 19 | 31 | 26 | 24 | 33 | 17 |
| 18 | 17 | 38 | 25 | 30 | 33 | 22 | 41 | 14 | 15 | 35 | 22 | 28 | 30 | 20 | 37 | 13 |
| 19 | 20 | 35 | 28 | 27 | 36 | 19 | 45 | 10 | 18 | 32 | 26 | 24 | 33 | 17 | 41 | 9 |
| 20 | 24 | 31 | 32 | 23 | 40 | 15 | 49 | 6 | 22 | 28 | 29 | 21 | 37 | 13 | 44 | 6 |
| 21 | 28 | 27 | 36 | 19 | 45 | 10 | 53 | 2 | 25 | 25 | 33 | 17 | 41 | 9 | 48 | 2 |
| 22 | 32 | 23 | 40 | 15 | 49 | 6 | | | 29 | 21 | 37 | 13 | 45 | 5 | | |
| 23 | 36 | 19 | 45 | 10 | 54 | 1 | | | 32 | 18 | 41 | 9 | 49 | 1 | | |

TABLE 2-continued

| Ti | % He | % Ar | % He | % Ar | | % He | % Ar | % He | % Ar | |
|---|---|---|---|---|---|---|---|---|---|---|
| 24 | 40 | 15 | 49 | 6 | | 36 | 14 | 45 | 5 | 5 |
| 25 | 45 | 10 | 54 | 1 | | 41 | 9 | 49 | 1 | |
| 26 | 49 | 6 | | | | 45 | 5 | | | |
| 27 | | | | | | | | | | |

TABLE 3

| | % O2 = 21 | | | | | | | | % O2 = 22 | | | | | |
|---|---|---|---|---|---|---|---|---|---|---|---|---|---|---|
| | TC = 35° C. | | TC = 34° C. | | TC = 33° C. | | TC = 32° C. | | TC = 35° C. | | TC = 34° C. | | TC = 33° C. | |
| Ti | % He | % Ar | % He | % Ar | % He | % Ar | % He | % Ar | % He | % Ar | % He | % Ar | % He | % Ar |
| 16 | 12 | 67 | 24 | 55 | 35 | 44 | 47 | 32 | 12 | 66 | 23 | 55 | 35 | 43 |
| 17 | 15 | 64 | 27 | 52 | 39 | 40 | 51 | 28 | 15 | 63 | 27 | 51 | 39 | 39 |
| 18 | 19 | 60 | 52 | 47 | 44 | 35 | 57 | 22 | 19 | 59 | 31 | 47 | 44 | 34 |
| 19 | 23 | 36 | 36 | 43 | 49 | 30 | 62 | 17 | 23 | 55 | 36 | 42 | 49 | 29 |
| 20 | 27 | 52 | 41 | 38 | 55 | 24 | 69 | 10 | 27 | 51 | 41 | 37 | 54 | 24 |
| 21 | 32 | 47 | 47 | 32 | 61 | 18 | 76 | 3 | 32 | 46 | 46 | 32 | 61 | 17 |
| 22 | 38 | 41 | 53 | 26 | 69 | 10 | | | 37 | 41 | 52 | 26 | 68 | 10 |
| 23 | 44 | 35 | 60 | 19 | 76 | 3 | | | 43 | 35 | 59 | 19 | 76 | 2 |
| 24 | 51 | 28 | 68 | 11 | | | | | 50 | 28 | 67 | 11 | | |
| 25 | 59 | 20 | 77 | 2 | | | | | 58 | 20 | 76 | 2 | | |
| 26 | 68 | 11 | | | | | | | 67 | 11 | | | | |
| 27 | 78 | 1 | | | | | | | 77 | 1 | | | | |

| | % O2 = 22 | | % O2 = 23 | | | | | | | |
|---|---|---|---|---|---|---|---|---|---|---|
| | TC = 32° C. | | TC = 35° C. | | TC = 34° C. | | TC = 33° C. | | TC = 32° C. | |
| Ti | % He | % Ar | % He | % Ar | % He | % Ar | % He | % Ar | % He | % Ar |
| 16 | 46 | 32 | 12 | 65 | 23 | 54 | 34 | 43 | 45 | 32 |
| 17 | 51 | 27 | 15 | 62 | 27 | 50 | 38 | 39 | 50 | 27 |
| 18 | 56 | 22 | 19 | 58 | 31 | 46 | 43 | 34 | 55 | 22 |
| 19 | 62 | 16 | 22 | 55 | 35 | 42 | 48 | 29 | 61 | 16 |
| 20 | 68 | 10 | 27 | 50 | 40 | 57 | 54 | 23 | 67 | 10 |
| 21 | 75 | 3 | 32 | 45 | 46 | 31 | 60 | 17 | 74 | 3 |
| 22 | | | 37 | 40 | 52 | 25 | 67 | 10 | | |
| 23 | | | 43 | 34 | 59 | 18 | 75 | 2 | | |
| 24 | | | 49 | 28 | 66 | 11 | | | | |
| 25 | | | 57 | 20 | 75 | 2 | | | | |
| 26 | | | 66 | 11 | | | | | | |
| 27 | | | 76 | 1 | | | | | | |

| | % O2 = 24 | | | | | | | | % O2 = 25 | | | | | |
|---|---|---|---|---|---|---|---|---|---|---|---|---|---|---|
| | TC = 35° C. | | TC = 34° C. | | TC = 33° C. | | TC = 32° C. | | TC = 35° C. | | TC = 34° C. | | TC = 33° C. | |
| Ti | % He | % Ar | % He | % Ar | % He | % Ar | % He | % Ar | % He | % Ar | % He | % Ar | % He | % Ar |
| 16 | 12 | 64 | 23 | 53 | 34 | 42 | 45 | 31 | 12 | 63 | 22 | 53 | 33 | 42 |
| 17 | 15 | 61 | 26 | 50 | 38 | 38 | 49 | 27 | 15 | 60 | 26 | 49 | 37 | 38 |
| 18 | 18 | 58 | 30 | 46 | 42 | 34 | 55 | 21 | 18 | 57 | 30 | 45 | 42 | 53 |
| 19 | 22 | 54 | 35 | 41 | 47 | 29 | 60 | 16 | 22 | 53 | 34 | 41 | 47 | 28 |
| 20 | 26 | 50 | 40 | 36 | 53 | 23 | 66 | 10 | 26 | 49 | 39 | 36 | 52 | 23 |
| 21 | 31 | 45 | 45 | 51 | 59 | 17 | 73 | 3 | 31 | 44 | 45 | 30 | 58 | 17 |
| 22 | 36 | 40 | 51 | 25 | 66 | 10 | | | 36 | 39 | 50 | 25 | 65 | 10 |
| 23 | 42 | 34 | 58 | 18 | 74 | 2 | | | 42 | 33 | 57 | 18 | 73 | 2 |
| 24 | 49 | 27 | 66 | 10 | | | | | 48 | 27 | 65 | 10 | | |
| 25 | 56 | 20 | 74 | 2 | | | | | 36 | 19 | 73 | 2 | | |
| 26 | 65 | 11 | | | | | | | 64 | 11 | | | | |
| 27 | 75 | 1 | | | | | | | 74 | 1 | | | | |

| | % O2 = 25 | | % O2 = 26 | | | | | | | |
|---|---|---|---|---|---|---|---|---|---|---|
| | TC = 32° C. | | TC = 35° C. | | TC = 34° C. | | TC = 33° C. | | TC = 32° C. | |
| Ti | % He | % Ar | % He | % Ar | % He | % Ar | % He | % Ar | % He | % Ar |
| 16 | 44 | 31 | 11 | 63 | 22 | 52 | 33 | 41 | 44 | 30 |
| 17 | 49 | 26 | 14 | 60 | 26 | 48 | 37 | 37 | 48 | 26 |
| 18 | 54 | 21 | 18 | 56 | 30 | 44 | 41 | 33 | 53 | 21 |
| 19 | 59 | 16 | 22 | 52 | 34 | 40 | 46 | 28 | 59 | 15 |
| 20 | 65 | 10 | 26 | 48 | 39 | 35 | 52 | 22 | 65 | 9 |
| 21 | 72 | 3 | 30 | 44 | 44 | 30 | 58 | 16 | 71 | 3 |
| 22 | | | 35 | 39 | 50 | 24 | 64 | 10 | | |

TABLE 3-continued

| Ti | | | | | | | | |
|---|---|---|---|---|---|---|---|---|
| 23 | 41 | 33 | 56 | 18 | 72 | 2 | | |
| 24 | 48 | 26 | 64 | 10 | | | | |
| 25 | 55 | 19 | 72 | 2 | | | | |
| 26 | 63 | 11 | | | | | | |
| 27 | 73 | 5 | | | | | | |

| | % O2 = 27 | | | | | | | | % O2 = 28 | | | | | |
|---|---|---|---|---|---|---|---|---|---|---|---|---|---|---|
| | TC = 35° C. | | TC = 34° C. | | TC = 33° C. | | TC = 32° C. | | TC = 35° C. | | TC = 34° C. | | TC = 33° C. | |
| Ti | % He | % Ar | % He | % Ar | % He | % Ar | % He | % Ar | % He | % Ar | % He | % Ar | % He | % Ar |
| 16 | 11 | 62 | 22 | 51 | 32 | 41 | 43 | 30 | 11 | 61 | 21 | 51 | 32 | 40 |
| 17 | 14 | 59 | 25 | 48 | 36 | 37 | 47 | 26 | 14 | 58 | 25 | 47 | 36 | 36 |
| 18 | 18 | 55 | 29 | 44 | 41 | 32 | 52 | 21 | 17 | 55 | 29 | 43 | 40 | 32 |
| 19 | 21 | 52 | 33 | 40 | 46 | 27 | 58 | 15 | 21 | 51 | 53 | 39 | 45 | 27 |
| 20 | 25 | 48 | 38 | 35 | 51 | 22 | 64 | 9 | 25 | 47 | 38 | 34 | 50 | 22 |
| 21 | 30 | 43 | 43 | 30 | 57 | 16 | 70 | 3 | 29 | 43 | 43 | 29 | 56 | 16 |
| 22 | 35 | 38 | 49 | 24 | 63 | 10 | | | 34 | 38 | 48 | 24 | 62 | 10 |
| 23 | 41 | 32 | 56 | 17 | 71 | 2 | | | 40 | 32 | 55 | 17 | 70 | 2 |
| 24 | 47 | 26 | 63 | 10 | | | | | 46 | 26 | 62 | 10 | | |
| 25 | 54 | 19 | 71 | 2 | | | | | 53 | 19 | 70 | 2 | | |
| 24 | 62 | 11 | | | | | | | 62 | 10 | | | | |
| 27 | 72 | 1 | | | | | | | 71 | 1 | | | | |

| | % O2 = 28 | | % O2 = 29 | | | | | | | | |
|---|---|---|---|---|---|---|---|---|---|---|---|
| | TC = 32° C. | | TC = 35° C. | | TC = 34° C. | | TC = 33° C. | | TC = 32° C. | | |
| Ti | % He | % Ar | % He | % Ar | % He | % Ar | % He | % Ar | % He | % Ar | |
| 16 | 42 | 30 | 11 | 60 | 21 | 50 | 31 | 40 | 42 | 29 | |
| 17 | 47 | 25 | 14 | 57 | 25 | 46 | 35 | 36 | 46 | 25 | |
| 18 | 52 | 20 | 17 | 54 | 28 | 43 | 40 | 31 | 51 | 20 | |
| 19 | 57 | 15 | 21 | 50 | 33 | 38 | 44 | 27 | 56 | 15 | |
| 20 | 63 | 9 | 25 | 46 | 37 | 34 | 50 | 21 | 62 | 9 | |
| 21 | 69 | 3 | 29 | 42 | 42 | 29 | 55 | 16 | 68 | 3 | |
| 22 | | | 34 | 57 | 48 | 23 | 62 | 9 | | | |
| 23 | | | 39 | 32 | 54 | 17 | 69 | 2 | | | |
| 24 | | | 46 | 25 | 61 | 10 | | | | | |
| 25 | | | 53 | 18 | 69 | 2 | | | | | |
| 24 | | | 61 | 10 | | | | | | | |
| 27 | | | 70 | 1 | | | | | | | |

| | % O2 = 30 | | | | | | | | % O2 = 35 | | | | | |
|---|---|---|---|---|---|---|---|---|---|---|---|---|---|---|
| | TC = 35° C. | | TC = 34° C. | | TC = 33° C. | | TC = 32° C. | | TC = 35° C. | | TC = 34° C. | | TC = 33° C. | |
| Ti | % He | % Ar | % He | % Ar | % He | % Ar | % He | % Ar | % He | % Ar | % He | % Ar | % He | % Ar |
| 16 | 11 | 59 | 21 | 49 | 31 | 39 | 41 | 29 | 10 | 55 | 19 | 46 | 29 | 36 |
| 17 | 14 | 56 | 24 | 46 | 35 | 35 | 46 | 24 | 13 | 52 | 23 | 42 | 32 | 33 |
| 18 | 17 | 53 | 28 | 42 | 39 | 31 | 50 | 20 | 16 | 49 | 26 | 39 | 36 | 29 |
| 19 | 20 | 50 | 32 | 38 | 44 | 26 | 55 | 15 | 19 | 46 | 30 | 35 | 41 | 24 |
| 20 | 24 | 46 | 37 | 33 | 49 | 21 | 61 | 9 | 23 | 42 | 34 | 31 | 45 | 20 |
| 21 | 29 | 41 | 42 | 28 | 54 | 16 | 67 | 3 | 27 | 38 | 39 | 26 | 51 | 14 |
| 22 | 33 | 37 | 47 | 23 | 61 | 9 | | | 31 | 34 | 44 | 21 | 56 | 9 |
| 23 | 39 | 31 | 53 | 17 | 68 | 2 | | | 36 | 29 | 50 | 15 | 63 | 2 |
| 24 | 45 | 25 | 60 | 10 | | | | | 42 | 23 | 56 | 9 | | |
| 25 | 52 | 18 | 68 | 2 | | | | | 48 | 17 | 63 | 2 | | |
| 26 | 60 | 10 | | | | | | | 56 | 9 | | | | |
| 27 | 69 | 1 | | | | | | | 64 | 1 | | | | |

| | % O2 = 35 | | % O2 = 40 | | | | | | | | |
|---|---|---|---|---|---|---|---|---|---|---|---|
| | TC = 32° C. | | TC = 35° C. | | TC = 34° C. | | TC = 33° C. | | TC = 32° C. | | |
| Ti | % He | % Ar | % He | % Ar | % He | % Ar | % He | % Ar | % He | % Ar | |
| 16 | 38 | 27 | 9 | 51 | 18 | 42 | 27 | 33 | 35 | 25 | |
| 17 | 42 | 23 | 12 | 48 | 21 | 39 | 30 | 30 | 39 | 21 | |
| 18 | 47 | 18 | 14 | 46 | 24 | 36 | 34 | 26 | 43 | 17 | |
| 19 | 51 | 14 | 18 | 42 | 28 | 32 | 37 | 23 | 47 | 13 | |
| 20 | 57 | 8 | 21 | 39 | 31 | 29 | 42 | 18 | 52 | 8 | |
| 21 | 63 | 2 | 25 | 35 | 36 | 24 | 47 | 13 | 58 | 2 | |
| 22 | | | 29 | 51 | 40 | 20 | 52 | 8 | | | |
| 23 | | | 33 | 27 | 46 | 14 | 58 | 2 | | | |

TABLE 3-continued

| | | | | |
|---|---|---|---|---|
| 24 | | 39 | 21 | 52 | 8 |
| 25 | | 44 | 16 | 59 | 1 |
| 26 | | 51 | 9 | | |
| 27 | | 59 | 1 | | |

| | % O2 = 45 | | | | | | | | % O2 = 50 | | | | | | | |
|---|---|---|---|---|---|---|---|---|---|---|---|---|---|---|---|---|
| | TC = 35° C. | | TC = 34° C. | | TC = 33° C. | | TC = 32° C. | | TC = 35° C. | | TC = 34° C. | | TC = 33° C. | | TC = 32° C. | |
| Ti | % He | % Ar | % He | % Ar | % He | % Ar | % He | % Ar | % He | % Ar | % He | % Ar | % He | % Ar | % He | % Ar |
| 16 | 8 | 47 | 16 | 39 | 24 | 31 | 32 | 25 | 8 | 42 | 15 | 35 | 22 | 28 | 29 | 21 |
| 17 | 11 | 44 | 19 | 36 | 27 | 28 | 36 | 19 | 10 | 40 | 17 | 33 | 25 | 25 | 33 | 17 |
| 18 | 13 | 42 | 22 | 33 | 31 | 24 | 39 | 16 | 12 | 38 | 20 | 30 | 28 | 22 | 36 | 14 |
| 19 | 16 | 39 | 25 | 30 | 34 | 21 | 43 | 12 | 15 | 35 | 23 | 27 | 31 | 19 | 40 | 10 |
| 20 | 19 | 36 | 29 | 26 | 38 | 17 | 48 | 7 | 17 | 33 | 26 | 24 | 35 | 15 | 44 | 6 |
| 21 | 23 | 32 | 33 | 22 | 43 | 12 | 53 | 2 | 20 | 30 | 30 | 20 | 39 | 11 | 48 | 2 |
| 22 | 26 | 29 | 37 | 18 | 48 | 7 | | | 24 | 26 | 34 | 16 | 43 | 7 | | |
| 23 | 31 | 24 | 42 | 13 | 53 | 2 | | | 28 | 22 | 38 | 12 | 48 | 2 | | |
| 24 | 35 | 20 | 47 | 8 | | | | | 32 | 18 | 43 | 7 | | | | |
| 25 | 41 | 14 | 54 | 1 | | | | | 37 | 13 | 49 | 1 | | | | |
| 26 | 47 | 8 | | | | | | | 43 | 7 | | | | | | |
| 27 | 54 | 1 | | | | | | | 49 | 1 | | | | | | |

The invention claimed is:

1. A method to administer to a patient a hypothermal inhalation gas composition, comprising:
   selecting a gas composition with 22% to 50% oxygen, 39% to 41% helium and 15 to 25% xenon; and
   administering the gas composition to the patient at an inhalation temperature between 19° C. and 21° C. in order to get a body temperature of the patient between 32° C. and 35° C.

2. The method of claim 1, wherein the step of administering the gas composition is performed via human-machine interface.

3. The method of claim 2, wherein the human-machine interface is a respiratory fan, a facial mask, or respiratory goggles.

4. The method of claim 1, further comprising a step of packaging the selected gas composition into a single container, wherein the packaging step is performed between the selecting step and the administering step.

5. The method according to claim 4, wherein oxygen, helium and xenon are packaged in the single container under a pressure between 10 and 300 bars.

6. A method to administer to a patient a hypothermal inhalation gas composition, comprising:
   selecting a gas composition with 22% to 30% oxygen, 39% to 57% helium and 15% to 35% xenon; and
   administering the gas composition to the patient at an inhalation temperature between 19° C. and 21° C. in order to get a body temperature of the patient between 32° C. and 35° C.

7. The method of claim 6, wherein the step of administering the gas composition is performed via human-machine interface.

8. The method of claim 7, wherein the human-machine interface is a respiratory fan, a facial mask, or respiratory goggles.

9. The method of claim 6, further comprising a step of packaging the selected gas composition into a single container, wherein the packaging step is performed between the selecting step and the administering step.

10. The method according to claim 9, wherein oxygen, helium and xenon are packaged in the single container under a pressure between 10 and 300 bars.

11. A method to administer to a patient a hypothermal inhalation gas composition, comprising:
   selecting a gas composition with 25% oxygen, 38% to 61% helium and 14% to 37% xenon; and
   administering the gas composition to the patient at an inhalation temperature between 19° C. and 21° C. in order to get a body temperature of the patient between 32° C. and 35° C.

12. The method according to claim 11, wherein the selected gas composition comprises 25% oxygen, 45% helium and 30% xenon.

13. The method of claim 11, wherein the step of administering the gas composition is performed via human-machine interface.

14. The method of claim 13, wherein the human-machine interface is a respiratory fan, a facial mask, or respiratory goggles.

15. The method of claim 11, further comprising a step of packaging the selected gas composition into a single container, wherein the packaging step is performed between the selecting step and the administering step.

16. The method according to claim 15, wherein oxygen, helium and xenon are packaged in the single container under a pressure between 10 and 300 bars.

17. A method to administer to a patient a hypothermal inhalation gas composition, comprising:
   selecting a gas composition with 22% to 30% oxygen, 32% to 55% helium and 16% to 41% argon; and
   administering the gas composition to the patient at an inhalation temperature between 19° C. and 21° C. in order to get a body temperature of the patient between 32° C. and 35° C.

* * * * *